(12) United States Patent
Hearn (10) Patent No.: US 10,524,844 B2
(45) Date of Patent: Jan. 7, 2020

(54) RATCHETING EPIPHYSIODESIS PLATE (75) Inventor: James P. Hearn, Coatsville, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 2335 days.

(21) Appl. No.: 12/665,201

(22) PCT Filed: Jun. 13, 2008

(86) PCT No.: PCT/US2008/066955
§ 371 (c)(1),
(2), (4) Date: Dec. 17, 2009

(87) PCT Pub. No.: WO2009/025925
PCT Pub. Date: Feb. 26, 2009

(65) Prior Publication Data
US 2010/0198221 A1    Aug. 5, 2010

Related U.S. Application Data (60) Provisional application No. 60/965,632, filed on Aug. 20, 2007.

(51) Int. Cl.
*A61B 17/80* (2006.01)

(52) U.S. Cl.
CPC ...... *A61B 17/8009* (2013.01); *A61B 17/8023* (2013.01)

(58) Field of Classification Search
CPC ...... A61B 17/7059; A61B 17/80–8023; A61B 17/8061; A61B 2017/681; A61B 2017/2837; Y10T 403/32434; Y10T 403/32426

USPC .......... 606/70, 71, 280–296; 403/103–109.8
See application file for complete search history.

(56) References Cited

U.S. PATENT DOCUMENTS

| | | | | |
|---|---|---|---|---|
| 3,604,414 A * | 9/1971 | Borges | | 606/105 |
| 5,372,598 A * | 12/1994 | Luhr | | A61B 17/8085 |
| | | | | 606/285 |
| 5,672,177 A * | 9/1997 | Seldin | | 606/71 |
| 5,827,286 A * | 10/1998 | Incavo et al. | | 606/71 |
| 6,852,113 B2 * | 2/2005 | Nathanson et al. | | 606/71 |
| 7,635,364 B2 * | 12/2009 | Barrall et al. | | 606/70 |
| 7,641,675 B2 * | 1/2010 | Lindemann et al. | | 606/282 |
| 7,645,295 B2 * | 1/2010 | Osman | | 606/281 |
| 7,749,256 B2 * | 7/2010 | Farris et al. | | 606/282 |
| 8,062,366 B2 * | 11/2011 | Melkent | | 623/17.11 |
| 8,795,342 B2 * | 8/2014 | Reisberg | | 606/324 |
| 2002/0183757 A1* | 12/2002 | Michelson | | A61B 17/7059 |
| | | | | 606/71 |
| 2003/0114856 A1 | 6/2003 | Nathanson et al. | | |

(Continued)

FOREIGN PATENT DOCUMENTS

DE    8624671    10/1986

*Primary Examiner* — Kevin T Truong
*Assistant Examiner* — Amy R Sipp
(74) *Attorney, Agent, or Firm* — Fay Kaplun & Marcin, LLP (57) ABSTRACT

A ratcheting epiphysiodesis plate comprises a female base half having a ratchet arm and a male sliding half having a series of ratchet teeth, the male sliding half being slidably connected to the female base half with the ratchet arm engaging the ratchet teeth, one of the female and male sliding halves including a first fixation element receiving hole for receiving therethrough a fixation element for binding the plate to a bone.

19 Claims, 5 Drawing Sheets

(56) References Cited

U.S. PATENT DOCUMENTS

| | | |
|---|---|---|
| 2003/0130661 A1 | 7/2003 | Osman |
| 2003/0175075 A1* | 9/2003 | Garrison ....................... 403/381 |
| 2004/0019353 A1* | 1/2004 | Freid .................. A61B 17/1728 606/915 |
| 2004/0111089 A1* | 6/2004 | Stevens .............. A61B 17/1728 606/86 B |
| 2005/0283155 A1 | 12/2005 | Jacene et al. |
| 2006/0089648 A1* | 4/2006 | Masini ............................ 606/69 |
| 2006/0235398 A1* | 10/2006 | Farris ................ A61B 17/7059 606/71 |
| 2007/0043371 A1* | 2/2007 | Teague .............. A61B 17/8076 606/71 |
| 2008/0188856 A1* | 8/2008 | Casutt ................... A61B 17/70 606/90 |
| 2008/0234681 A1* | 9/2008 | Baynham ....................... 606/71 |

* cited by examiner

RATCHETING EPIPHYSIODESIS PLATE

PRIORITY CLAIM

The present application is a 371 application of PCT Application Serial No. PCT/US2008/066955 filed on Jun. 13, 2008; which claims the benefit of U.S. Provisional Application Ser. No. 60/965,632 filed on Aug. 20, 2007. The disclosure of the above patent(s)/application(s) is incorporated herein by reference.

TECHNOLOGY FIELD

The invention relates generally to a plate for correction of deformities of growth plates of bones. More particularly, the invention relates to a ratcheting epiphysiodesis plate and a method of treating deformities of the growth plate using the ratcheting epiphysiodesis plate.

BACKGROUND

In children, a growth plate will sometimes grow faster on one side than the other causing an angular or rotational deformity of the bone. Traditional methods of treating angular deformities of the growth plate include insertion of staples, k-wires, or screws into the growth plate to restrain or temporarily arrest growth on one side while allowing the other side to grow and correct the angular deformity. In some instances, however, the restricted side of the growth plate may fuse closed while the other side of the growth plate is still growing, thereby resulting in a deformity in the opposite direction.

SUMMARY OF THE INVENTION

This summary is provided to introduce a selection of concepts in a simplified form that are further described below in the Detailed Description of Illustrative Embodiments. This Summary is not intended to identify key features or essential features of the invention, nor is it intended to be used to limit the scope of the invention.

The invention provides a ratcheting epiphysiodesis plate that restricts the growth of a growth plate without fusing the growth plate closed. According to one embodiment, the expanding plate comprises a female base half, a male sliding half and a slider band. The male half is slidably received in the female half such that the male half can translate with respect to the female base half along a longitudinal axis of the plate.

In one embodiment, the female base half includes a first end, a second end, a cavity, a ratchet arm and a hole. The cavity is disposed along a longitudinal axis of the female base half and defines an opening at the first end of the female base half. The ratchet arm is disposed adjacent and substantially parallel to the cavity. The hole is disposed at the second end of the female base half and adapted to receive a fastener for securing the female base half to a bone.

In one embodiment, the male sliding half includes a first end, a second end, a plurality of ratchet teeth and a hole. The first end of the male sliding half is shaped to be inserted into the opening on the first end of the female base half and slid into the cavity. The hole is disposed at the second end of the male sliding half and adapted to receive a fastener for securing the male sliding half to a bone. The ratchet teeth are disposed along a longitudinal axis and adapted to engage the ratchet arm so that the male and female halves can translate with respect to each other along a longitudinal axis. Thus, the ratcheting epiphysiodesis plate can be lengthened or shortened along the longitudinal axis.

In one embodiment, the slider band is disposed around the female base half and over the ratchet arm such that the slider band can be slid along the ratchet arm in a longitudinal direction. Thus, by sliding the slider band along the ratchet arm, the effective length of the ratchet arm may be set. According to another embodiment, the ratcheting epiphysiodesis plate may be provided with a selection of female base halves having different length ratchet arms rather than a single female base half with a slider band that can be set to produce different effective lengths of the ratchet arm. The length of the ratchet arm determines the preset load required to release the ratchet teeth from the ratchet arm.

The invention is also directed to a method of treating a deformity of the growth plate with a ratcheting epiphysiodesis plate. In one implementation, an appropriate preset load for the ratcheting mechanism is determined and the ratcheting epiphysiodesis plate is configured accordingly as described above. The overall length of the ratcheting epiphysiodesis plate may be adjusted to accommodate various growth plate dimensions by sliding the male sliding half with respect to the female base half and advancing the ratcheting mechanism. Once the ratcheting epiphysiodesis plate has been properly configured, it may be disposed across a portion of the growth plate and secured to the bone by inserting fasteners through the holes in the female and male halves of the ratcheting epiphysiodesis plate.

The present invention is directed to a ratcheting epiphysiodesis plate comprises a female base half having a ratchet arm and a male sliding half having a series of ratchet teeth, the male sliding half being slidably connected to the female base half with the ratchet arm engaging the ratchet teeth, one of the female and male sliding halves including a first fixation element receiving hole for receiving therethrough a fixation element for binding the plate to a bone.

Additional features and advantages of the invention will be made apparent from the following detailed description of illustrative embodiments that proceeds with reference to the accompanying drawings.

BRIEF DESCRIPTION OF THE DRAWINGS

The foregoing summary, as well as the following detailed description of the preferred embodiments, is better understood when read in conjunction with the appended drawings. For the purpose of illustrating the invention, there are shown in the drawings embodiments that are presently preferred, it being understood, however, that the invention is not limited to the specific methods and instrumentalities disclosed. In the drawings.

DETAILED DESCRIPTION

The present invention is directed to an expanding plate 10 for treating angular and/or rotational deformities of the growth plate. It should be noted, however, that although the exemplary embodiments of the present invention are described using directional references (e.g., top, bottom, front, back, side), the directional references used herein do not define any specific direction, but refer to surfaces relative to the plate 10. For example, a bottom refers to a bone-facing surface, a top refers to a surface facing away from the bone, a front refers to a first longitudinal end while a back refers to a second longitudinal end, and a side refers to a surface of the plate 10 along a longitudinal axis of the plate 10.

Figure 1:
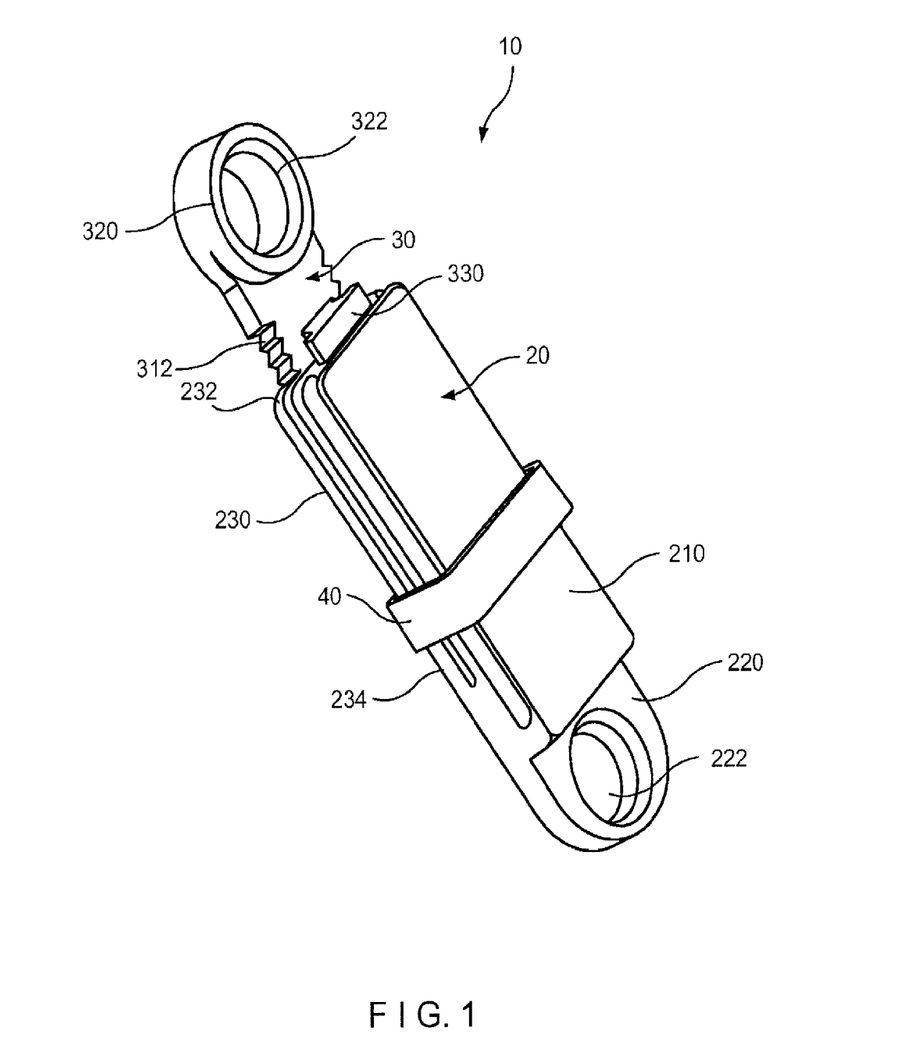
FIG. 1 shows a top perspective view of an exemplary expanding plate.
Figure 2:
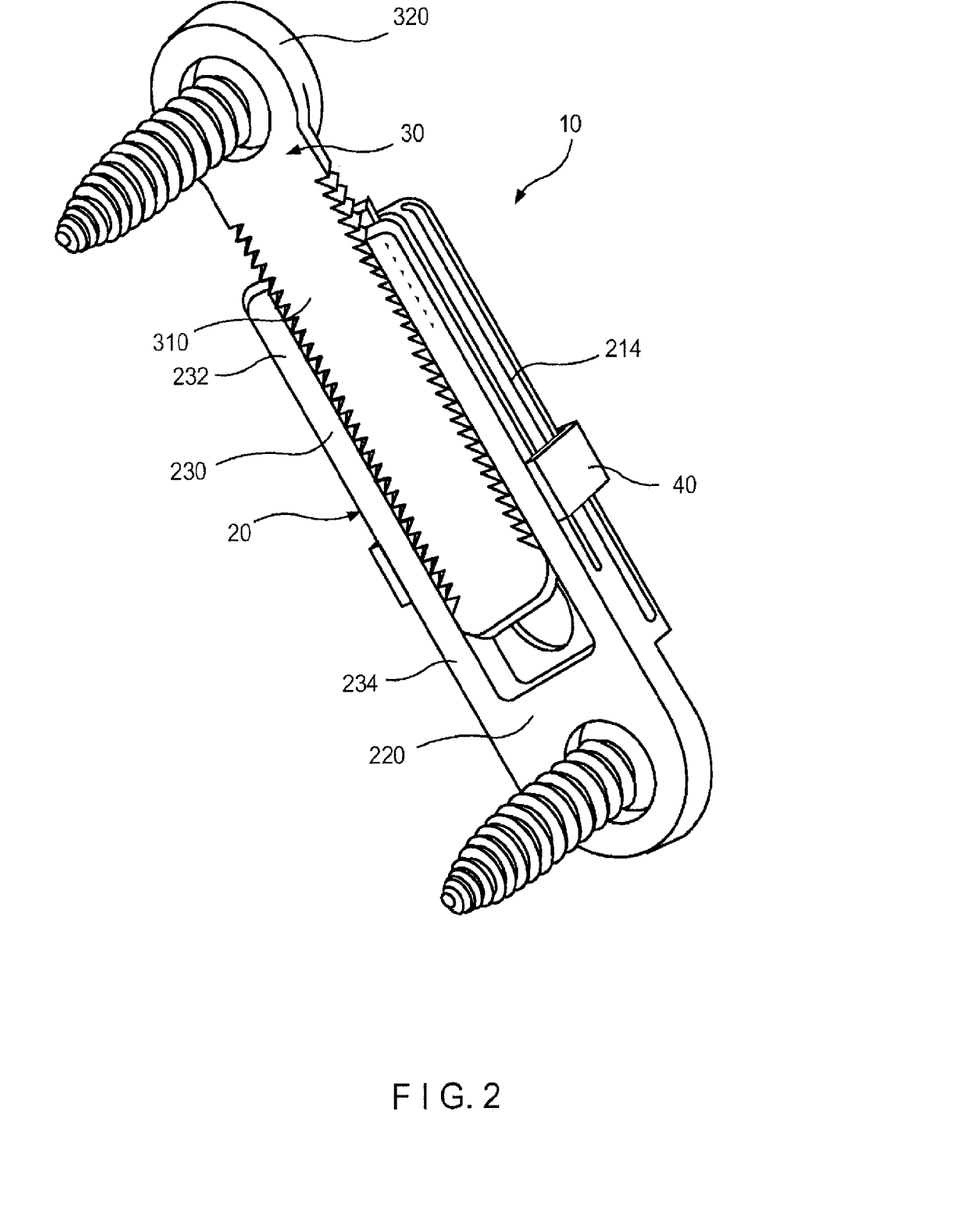
FIG. 2 shows a bottom perspective view of the expanding plate shown in FIG. 1.

In one embodiment, as shown in FIGS. 1 and 2, the expanding plate 10 comprises a female base half 20, a male sliding half 30, and a slider hand 40. The male half 30 is slidably received in the female half 20 such that the female 20 and male 30 halves can translate with respect to each other along a longitudinal axis. The slider band 40 wraps around a top 206 and side portions 208a, 208b of the female half 20. Alternatively, in another embodiment, the expanding plate 10 may be configured without the slider band 40.

According to one embodiment, the female half 20 comprises an elongate body section 210, a head section 220 and ratchet arms 230. The body section 210 extends longitudinally from a first end 216 to a second end 218. The head section 220 which may, for example, be integrally formed with the body section 210 extends from the second longitudinal end 218. The ratchet arm 230 may be disposed on a bottom 202 of the body section 210 extending substantially parallel to a longitudinal axis of the body section 210. Although the body section 210, head section 220, and ratchet arms 230 of the female half 20 will be described as separate elements, it is understood that they may be integrally formed as one unit. Furthermore, it will be understood by those skilled in the art, that the ratchet arms 230 extend along an axis which, when the plate 10 is mounted to the bone in a desired orientation, extends substantially parallel to an axis along which it is desired to apply tension or compression to the bone without regard to any axis of the body section 210 or the plate 10 itself.

The body section 210 extends from the first end 216 to the second end 218 and may have a substantially rectangular shape. The body section 210 includes a cavity 212 extending longitudinally therethrough and which may be open to the bottom 202 and the first longitudinal end 216 of the body section 210. A cross-sectional profile (i.e., transverse to the longitudinal axis of the body section 210) of an opening 204 at the bottom 202 may be narrower than a cross-sectional profile of the cavity 212 at any other portion, as best shown in FIG. 5. Thus, for example, the cross-sectional profile of the cavity 212 may be T-shaped, V-shaped, or any other suitable shape. However, it will be understood by those of skill in the art that the cavity 212 may take any size and shape so long as a cross-sectional profile of the opening 204 of the cavity 212 is narrower than the cavity 212. Also, as shown in FIGS. 3 and 4, the sides of the body section 210 may include grooves 214 extending longitudinally along the body section 210.

Figure 3:
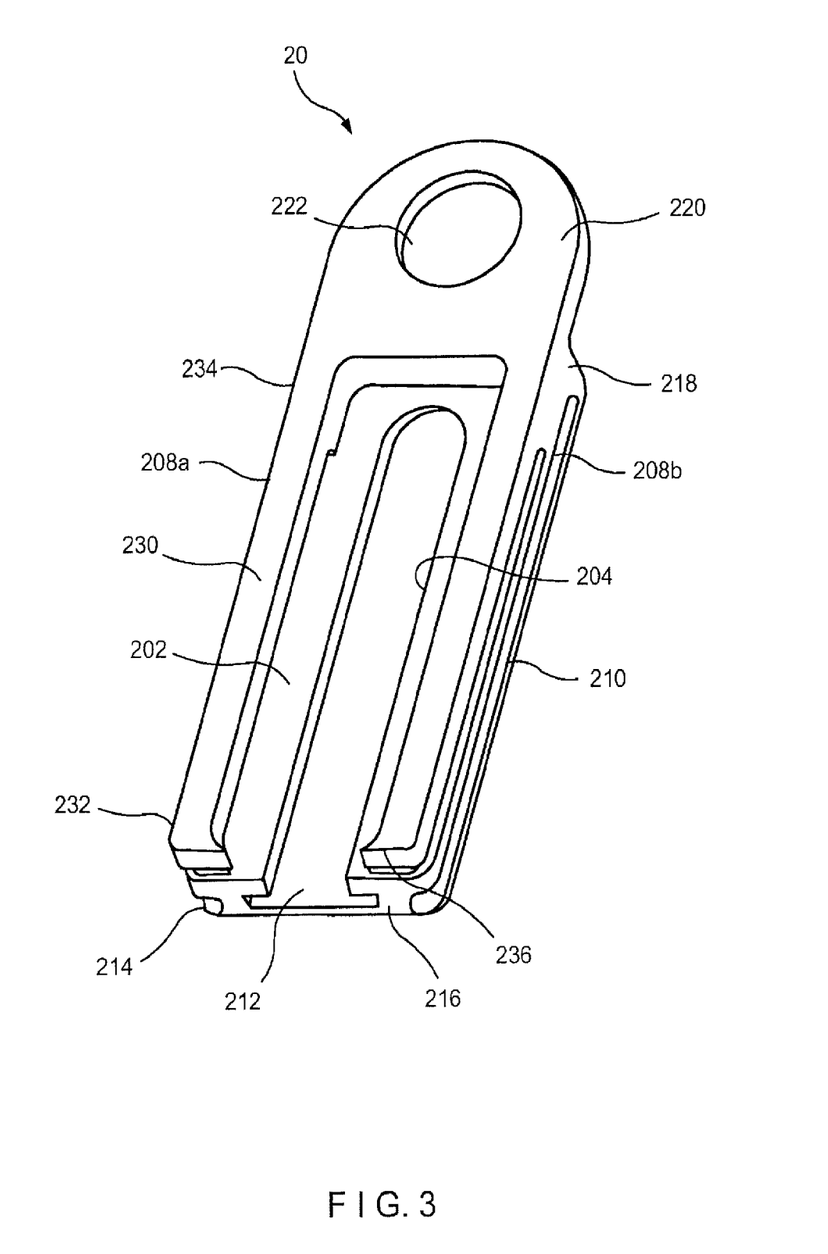
FIG. 3 shows a bottom perspective view of an exemplary female half.

As shown in FIG. 3, the head section 220 of the female half 20 defines at least one fixation element receiving hole 222 adapted to receive therethrough a screw or other fixation element to secure the plate 10 to a bone. Also, although not shown, the portion of the head section 220 connected to the body section 210 may be adapted to be bent so that the head section 220 may be disposed in different orientations with respect to the body section 210 as desired to adapt the plate 10 to the anatomy of a target site. Preferably, the female half 20 is adapted to be bent by providing a suitable material in a portion thereof that joins the body 210 to the head section 220 or by providing a suitable geometry for the portion that joins the body 210 and head section 220 or a combination of both. For example, the body 210 and the head section 220 may be joined by a hinge permitting the body 210 and the head 220 to pivot relative to one another thereabout. Alternatively, the body 210 and the head section 220 may be joined by a flexible material that may be bent into a desired configuration.

Figure 4:
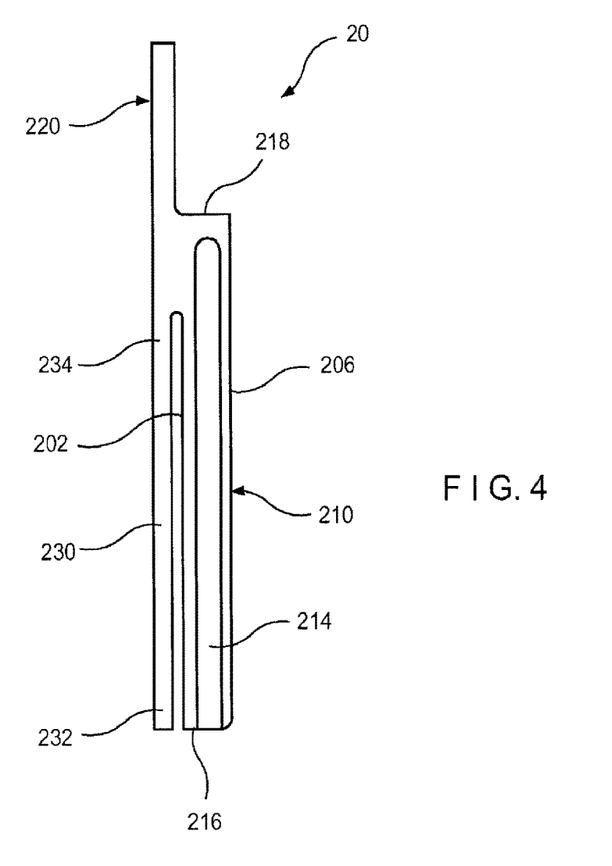
FIG. 4 shows a side view of the female half shown in FIG. 3.
Figure 5:
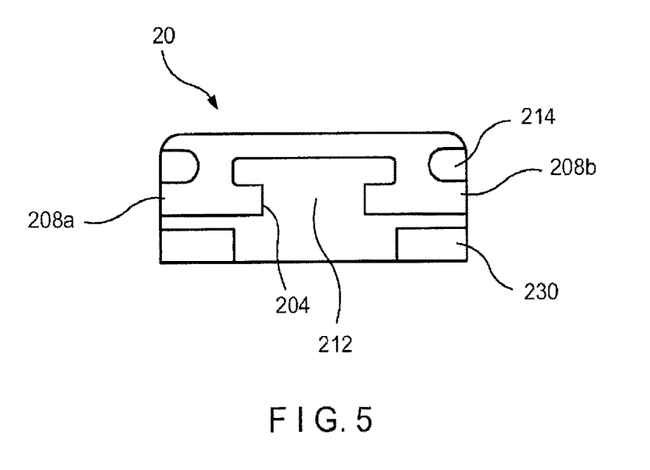
FIG. 5 shows a front view of the female half shown in FIG. 3.

As shown in FIGS. 3-5, the ratchet arms 230 have elongate bodies with front ends 232 and back 234 ends. As shown, the ratchet arms 230 are disposed on the bottom 202 of the body section 210 and adjacent to the sides of the body section 210 such that the front end 232 is adjacent to the first longitudinal end 216 while the back end 234 is adjacent to the second longitudinal end 218. The back ends 234 of the ratchet arms 230 may attached to the body section 210 on the bottom 204 at the second end 218. As shown, the ratchet arms 230 are only connected to the body section 210 at the back ends 234 and the front ends 232 of the ratchet arms 230 are able to flex outwardly to the sides. The tip of each of the front ends 232 of the ratchet arms 230 may have a pawl 236 inwardly oriented, relative to a longitudinal axis of the body section 210. It will be understood by those of skill in the art, however, that one of the front ends 232 of the ratchet arms 230 may include the pawl 236 while the other front end 232 does not. It will also be understood by those of skill in the art, that although FIGS. 1-5 show the female half 20 with two ratchet arms 230, in an alternative embodiment, the female half 20 may include only one ratchet arm 230.

Figure 6:
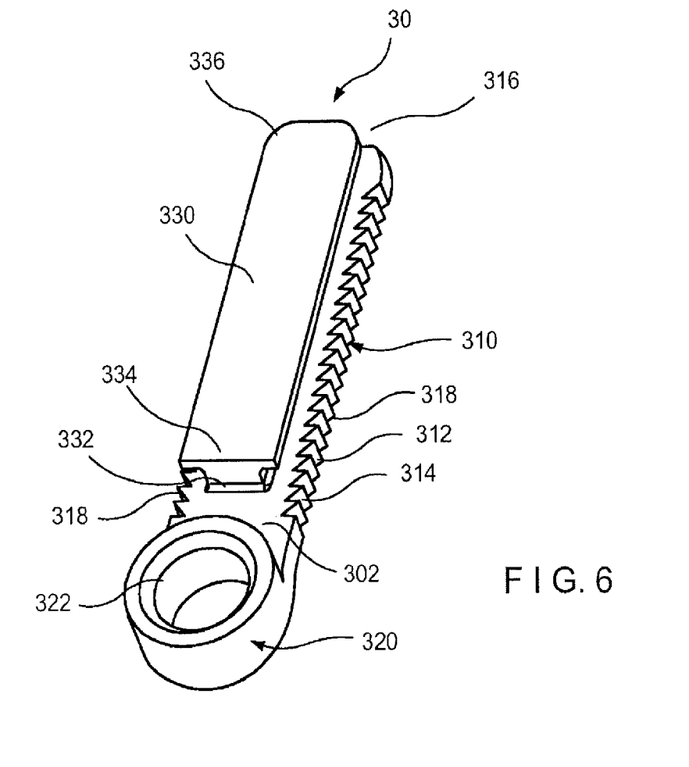
FIG. 6 shows top perspective view of an exemplary male half.

According to one embodiment, shown in FIG. 6, the male half 30 comprises an elongate body section 310, a head section 320 and a fin 330. The body section 310 extends longitudinally from a first end 314 to a second end 316 with a head section 320 extending from the first end 314. As with the plate 10, the head section 320 may be integrally formed with the body section 310. The fin 330 may be disposed on a top 302 of the body section 310 such that it is integrally formed with the body section 310. Although the body section 310, head section 320, and fin 330 of the male half 30 will be described as separate elements, it is understood that they may be formed as one unit.

In the embodiment shown, the body section 310 is substantially rectangular with lateral edges 318 thereof including a series of ratchet teeth 312. As shown in FIG. 6, a portion of the lateral edges 318 adjacent to the second end 316 may include no ratchet teeth 312. It will be understood by those skilled in the art that, although the ratchet teeth 312 are formed on both lateral edges 318, in an alternative embodiment, the ratchet teeth 312 may be formed on only one of the lateral edges 318 in a number corresponding to a number of ratchet arms 230 and/or pawls 236 of the ratchet arms 230.

As shown in FIG. 6, the head section 320 of the male half 30 defines at least one hole 322 adapted to receive a screw or other fixation element to secure the plate 10 to a bone. Also, although not shown, the portion of the head section 320 connected to the body section 310 may be adapted to be bent so that the head section 320 may be disposed in different orientations with respect to the body section 310. Preferably, the male half 30 is adapted to be bent by providing a suitable material in a portion joining the body 310 to the head section 320, by providing a suitable geometry for the portion joining the body 310 and head section 320, or through a combination of both. For example, the body 310 and the head 320 may be joined by a hinge such that the body 210 and the head 320 may pivot thereabout relative to one another. Alternatively, the body 310 and the head 320 may be joined by a flexible material that may be bent to a desired configuration.

Figure 7:
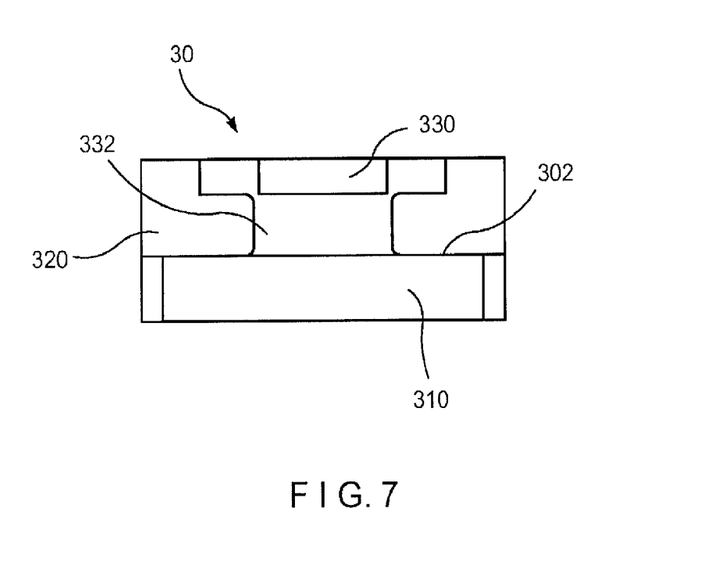
FIG. 7 shows a front view of the male half shown in FIG. 6.

The fin 330 is disposed on the top 302 of the body section 310 extending along a longitudinal axis of the body section 310 from a first end 334 to a second end 336 thereof. The fin 330 may be connected to the body section 310 via a connecting portion 332. In a preferred embodiment, as best shown in FIG. 7, a cross sectional profile (i.e., transverse to the longitudinal axis) of the connecting portion 332 may be narrower than the fin 330. Thus, for example, the cross-sectional profile of the fin 330 and the connecting portion 332 may be T-shaped, V-shaped, or any other suitable shape. The cross-sectional profile of the fin 330 may be shaped and dimensioned such that it dovetails with the cross-sectional profile of the cavity 212 of the female half 20. In other words, the fin 330 may be received within the cavity 212 such that the connecting portion 332 may be accommodated within the bottom opening of the cavity 212. Thus, it will be understood by those of skill in the art that the fin 330 may be of any shape and size so long as the fin 330 corresponds to the cavity 212 and the connecting portion 332 corresponds to the bottom opening 204.

Referring back to FIGS. 1 and 2, according to one embodiment a slider hand 40 is disposed over the female half 20 wrapping around the top 206 and sides 208a, 208b of the body section 210. The slider band 40 engages the grooves 214 on the sides of the body section 210 such that the slider band 40 may slide longitudinally along the longitudinal axis of the body section 210 between the first and second ends 216, 218, respectively. The male half 30 and the female half 20 are assembled by sliding the second end 336 of the fin 330 into the first end 216 of the cavity 212 such that the pawls 236 of the ratchet arms 230 engage the ratchet teeth 312. According to one embodiment, a portion on the lateral edges 318 at the second end 316 may have no ratchet teeth 312, so that portion can be slid into the female half 20 without resistance. Thus, the male half 30 may be inserted and stabilized in the female half 20 before the pawls 236 of the ratchet arms 230 engage the ratchet teeth 312. Further, the configuration of the fin 330 and the cavity 212 ensures that female and male halves 30, 20, respectively, may slide with respect to each other along a longitudinal axis without separating otherwise.

The ratchet teeth 312 and the pawl 236 are configured such that the male and female halves 30, 20, respectively, may move with respect to each other along a longitudinal axis allowing the plate 10 to be lengthened or shortened along the longitudinal axis as desired. The male half 30 is released with respect to the female half 20 to allow longitudinal expansion of the plate 10 at a preset load. According to one embodiment, the preset load may be adjusted by adjusting the position of the slider band 40 over ratchet arms 230 on the female half 20. By changing the position of the slider band 40, the length of the portion of the ratchet arm 230 that can flex outwardly may be lengthened or shortened. Thus, the preset load required to release the ratchet teeth 312 from the pawls 236 on the ratchet arm 230 may be adjusted. The ratchet teeth 312 and the ratchet arm 230 with its pawls 236 may be collectively referred to as the ratcheting mechanism. In another embodiment, the expanding plate 10 does not incorporate a slider band 40 and the female half 20 may be selected from a variety of female halves 20 having ratchet arms 230 of various lengths. Thus, a male half 30 may be combined with one of a variety of female halves 20 to achieve an expanding plate 10 having a ratcheting mechanism with a desired preset load.

Another aspect of the invention is directed to a method of treating a growth plate with a ratcheting epiphysiodesis plate as described above. There are particular considerations for aligning and/or positioning the ratcheting epiphysiodesis plate over the growth plate, which depend on the particular situation for which the plate is to be employed (e.g., a type of deformity to be corrected). The position of the ratcheting epiphysiodesis plate dictates the type of correction to be effectuated. For example, for a valgus deformity for which a varus correction is to be undertaken, a ratcheting epiphysiodesis plate as described above may be placed on the medial side of the bone to restrict growth thereof. When a rotational correction is necessary, two or more ratcheting epiphysiodesis plates may be placed on an angle across the growth plate. These ratcheting epiphysiodesis plates cause rotation of the segments of the bone as the growth plate grows until the ratcheting epiphysiodesis plates become axially aligned with the bone. The degree of rotation will depend on the length of the plates and the angle of the initial placement.

According to one implementation, an appropriate preset load for the ratcheting mechanism is determined and the ratcheting mechanism is configured to obtain this load as described above. The ratcheting epiphysiodesis plate may be disposed across a portion of the growth plate and attached to the bone at least 5 mm to 8 mm from the growth plate. Otherwise, there is a risk of disrupting the growth plate and causing premature closure or fusion of the growth plate. Thus, the overall length of the ratcheting epiphysiodesis plate may be adjusted to accommodate various growth plate dimensions by sliding the male sliding half with respect to the female base half and advancing the ratcheting mechanism.

Once the load of the ratcheting mechanism and the overall length ratcheting epiphysiodesis plate have been set, the ratcheting epiphysiodesis plate may be secured to the bone by inserting fixation elements (e.g., bone pins and/or screws) through the holes in the female and male halves of the ratcheting epiphysiodesis plate. The ratcheting epiphysiodesis plate allows the growth plate to grow to the extent that the growth can overcome the preset load of the ratcheting mechanism of the ratcheting epiphysiodesis plate. Thus, the ratcheting epiphysiodesis plate may be used to restrict the growth of a growth plate and correct a deformity without fusing the growth plate closed.

It will be apparent to those skilled in the art that various modifications and variations can be made in the structure and methodology of the present invention, without departing from the spirit and scope of the invention. Thus, it is intended that the present invention cover the modifications and variations of this invention provided that they come within the scope of the appended claims and their equivalents.

What is claimed:

1. A ratcheting epiphysiodesis plate comprising:
    a female base half having a ratchet arm;
    a male sliding half having a series of ratchet teeth, the male sliding half being slidably connected to the female base half with the ratchet arm engaging the series of ratchet teeth, one of the female base half and male sliding half including a first fixation element receiving hole for receiving therethrough a fixation element for binding the plate to a bone; and
    a slider band slidably connected to the female base half for movement relative thereto along a longitudinal axis of the ratchet arm to change an effective length of a deflectable portion of the female base half, the slider band being disposed over the ratchet arm, the effective length of the deflectable portion of the female base half determined by the position of the slider band controlling a deflection of the ratchet arm of the female base half to control a preset load at which the male sliding half will disengage from the ratchet arm to permit relative movement between the female base half and the male sliding half.

2. The ratcheting epiphysiodesis plate of claim 1, wherein the female base half includes a female head section extending from an end of a female base portion.

3. The ratcheting epiphysiodesis plate of claim 2, wherein the first fixation element receiving hole extends through the female head section.

4. The ratcheting epiphysiodesis plate of claim 2, wherein the female head section is coupled to the female base portion via a female linkage permitting angulation of the female half head section relative to the female base portion about an axis substantially perpendicular to a longitudinal axis of the plate.

5. The ratcheting epiphysiodesis plate of claim 4, wherein the female linkage includes a coupling formed of a material having increased flexibility relative to a material of which the female base portion is formed.

6. The ratcheting epiphysiodesis plate of claim 4, wherein the female linkage includes a hinge pivotally coupling the female head section to the female base portion.

7. The ratcheting epiphysiodesis plate of claim 4, wherein the female linkage includes a bending area having a thickness reduced relative to a thickness of the female base portion.

8. The ratcheting epiphysiodesis plate of claim 1, wherein the male sliding half comprises a male head section extending from an end of a male base portion.

9. The ratcheting epiphysiodesis plate of claim 8, wherein the first fixation element receiving hole is formed in the male head section.

10. The ratcheting epiphysiodesis plate of claim 8, wherein the male head section is coupled to the male base portion via a male linkage permitting angulation of the male head section relative to the male base portion about an axis substantially perpendicular to a longitudinal axis of the plate.

11. The ratcheting epiphysiodesis plate of claim 10, wherein the male linkage includes a coupling formed of a material having increased flexibility relative to a material of which the male base portion is formed.

12. The ratcheting epiphysiodesis plate of claim 10, wherein the male linkage includes a hinge pivotally coupling the male head section to the male base portion.

13. The ratcheting epiphysiodesis plate of claim 10, wherein the male linkage includes a bending area having a thickness reduced relative to a thickness of the male base portion.

14. The ratcheting epiphysiodesis plate of claim 1, wherein the female base half further comprises an elongate cavity extending therein substantially parallel to a longitudinal axis of the female half.

15. The ratcheting epiphysiodesis plate of claim 14, wherein the male sliding half further comprises an elongate fin sized and shaped to be slidably received in the elongate cavity of the female base half, the elongate fin extending substantially parallel to a longitudinal axis of the male sliding half.

16. The ratcheting epiphysiodesis plate of claim 14, wherein the elongate cavity has a cross-section transverse to the longitudinal axis of the female base half narrower at a first end thereof than at a second end thereof.

17. The ratcheting epiphysiodesis plate of claim 16, wherein the male sliding half further comprises an elongate fin sized and shaped to be slidably received in the elongate cavity of the female base half, the elongate fin extending substantially parallel to a longitudinal axis of the male sliding half and having a cross-section transverse to the longitudinal axis of the male sliding half corresponding to the cross-section of the elongate cavity.

18. A method of treating a bone comprising:
   a) setting to a desired level, via a slider band, a preset load at which a ratcheting mechanism of an epiphysiodesis plate will disengage to permit relative movement between female and male base halves thereof, the slider band controlling deflection of a ratchet atm of the female base half;
   b) setting to a desired position a relative position of the male base half relative to the female base half; and
   c) coupling the ratcheting epiphysiodesis plate in a desired position across a growth plate of a bone to be treated; and
   d) adjusting the preset load by moving the slider band slidably connected to the female base half along a longitudinal axis of the ratchet arm, the slider being disposed over the ratchet arm, wherein moving the slider band along a longitudinal axis of the ratchet arm changes an effective length of a deflectable portion of the female base half.

19. The method of claim 18, wherein the female base half and the male sliding base half are secured to the bone about 5 mm-8 mm from the growth plate.

* * * * *